United States Patent
Amschler et al.

(10) Patent No.: US 10,880,932 B2
(45) Date of Patent: Dec. 29, 2020

(54) CENTRAL PRIORITY ADVERTISEMENT FOR MEDICAL DEVICES

(71) Applicant: PHILIPS HEALTHCARE INFORMATICS, INC., Cambridge, MA (US)

(72) Inventors: John Earl Amschler, San Diego, CA (US); Taun Chapman, West Chester, PA (US)

(73) Assignee: Koninklijke Philips N.V., Eindhoven (NL)

( * ) Notice: Subject to any disclaimer, the term of this patent is extended or adjusted under 35 U.S.C. 154(b) by 596 days.

(21) Appl. No.: 15/713,532

(22) Filed: Sep. 22, 2017

(65) Prior Publication Data

US 2018/0235016 A1  Aug. 16, 2018

Related U.S. Application Data

(60) Provisional application No. 62/459,527, filed on Feb. 15, 2017.

(51) Int. Cl.
| | |
|---|---|
| *H04W 76/11* | (2018.01) |
| *H04W 4/02* | (2018.01) |
| *G06F 19/00* | (2018.01) |
| *H04W 8/00* | (2009.01) |
| *H04W 76/23* | (2018.01) |
| *G16H 40/67* | (2018.01) |
| *A61B 5/00* | (2006.01) |
| *H04W 48/10* | (2009.01) |
| *H04W 88/06* | (2009.01) |

(Continued)

(52) U.S. Cl.
CPC ......... *H04W 76/11* (2018.02); *G06F 19/3418* (2013.01); *G16H 40/67* (2018.01); *H04W 4/02* (2013.01); *H04W 8/005* (2013.01); *H04W 76/23* (2018.02); *A61B 5/0022* (2013.01); *H04W 48/10* (2013.01); *H04W 48/16* (2013.01); *H04W 84/20* (2013.01); *H04W 88/06* (2013.01)

(58) Field of Classification Search
None
See application file for complete search history.

(56) References Cited

U.S. PATENT DOCUMENTS

| 8,799,492 B2 | 8/2014 | Iinuma |
| 9,301,087 B1 | 3/2016 | Pappas et al. |

(Continued)

FOREIGN PATENT DOCUMENTS

| EP | 2306692 A1 | 4/2011 |
| EP | 2884776 A2 | 6/2015 |
| EP | 3125641 A1 | 2/2017 |

OTHER PUBLICATIONS

International Search Report and Written Opinion—PCT/US2017/068182—ISA/EPO—dated Mar. 16, 2018.

(Continued)

*Primary Examiner* — Michael Tomaszewski

(57) ABSTRACT

Techniques are disclosed for enabling a first central device to connect with a medical device with an existing connection to a second central device by broadcasting a "central priority" advertisement packet that causes the second central device to discontinue attempts to connect with the medical device (for a period of time), granting the first central device the ability to establish communication with the medical device.

33 Claims, 5 Drawing Sheets

(51) Int. Cl.
  *H04W 48/16*    (2009.01)
  *H04W 84/20*    (2009.01)

(56) References Cited

U.S. PATENT DOCUMENTS

| | | |
|---|---|---|
| 2015/0201455 A1* | 7/2015 | Redding ................ H04W 4/80 |
| | | 455/41.2 |
| 2015/0244715 A1 | 8/2015 | Narayan et al. |
| 2015/0245194 A1 | 8/2015 | Kim et al. |
| 2016/0085922 A1* | 3/2016 | Sweeney ................ G16H 70/00 |
| | | 705/2 |
| 2016/0277878 A1 | 9/2016 | Lee |
| 2017/0011608 A1 | 1/2017 | Wilging |
| 2017/0093727 A1 | 3/2017 | Chen et al. |

OTHER PUBLICATIONS

International Preliminary Report on Patentability—PCT/US2017/068182—ISA/EPO—dated Aug. 29, 2019.
International Preliminary Report on Patentability—PCT/US2018/018487—ISA/EPO—dated Aug. 29, 2019.

* cited by examiner

CENTRAL PRIORITY ADVERTISEMENT FOR MEDICAL DEVICES

RELATED APPLICATIONS

This application claims the benefit of U.S. Provisional Application No. 62/459,527, filed Feb. 15, 2017, entitled "TECHNIQUES FOR DETERMINING CONNECTION PRIORITY TO A DEVICE", which is assigned to the assignee hereof, and incorporated by reference herein in its entirety.

BACKGROUND

Medical devices for home use by a patient have recently become modified to track and report related usage data, which can be sent wirelessly to, for example, a smart phone of a user. Wireless technologies used to convey this data, such as Bluetooth® Low Energy (BLE), may create a central/peripheral relationship where the mobile device is the central and the medical device is the peripheral.

This central/peripheral relationship can prevent other devices from connecting with the medical device. This can present an issue when, for example, a health care provider attempts to connect a device to the medical device (e.g., to extract data from the medical device). If the patient's mobile device is nearby, it may prevent the device of the health care provider from connecting with the medical device.

SUMMARY

Techniques provided herein address these and other issues by enabling a first central device (e.g., a health care provider's device) to connect with the medical device by broadcasting a "central priority" advertisement packet that causes a second central device (e.g., the patient's device) to discontinue attempts to connect with the medical device for a period of time. This enables the first central device to establish communication the medical device.

An example method enabling connection priority determination in a medical device, according to the description, comprises determining, with a first central device, a triggering event has occurred, and in response to determining the triggering event has occurred, wirelessly broadcasting a first advertisement packet from the first central device, the first advertisement packet configured to cause a second central device to enter a hold off state for a period of time. The method further comprises wirelessly receiving, during the period of time, a second advertisement packet at the first central device, the second advertisement packet sent from the medical device, and in response to receiving the second advertisement packet, establishing a wireless communication session between the first central device and the medical device.

Embodiments of the method may comprise one or more of the following features. The method may further comprise receiving at the first central device, prior to receiving the second advertisement packet, an acknowledgment from the second central device that the second central device received the first advertisement packet. The first advertisement packet may include information indicating a length of the period of time. The first advertisement packet may include an identifier of the medical device. The method may further comprise obtaining the identifier of the medical device using a camera of the first central device. Determining the triggering event has occurred may comprise determining a user input has been received by the first central device. Determining the triggering event has occurred may comprise determining a location of the first central device is within a particular locale.

An example central device, according to the description, comprises a wireless communication interface, a memory, and a processing unit communicatively coupled with the wireless communication interface and the memory. Processing unit is configured to cause the central device to determine a triggering event has occurred, and in response to determining the triggering event has occurred, wirelessly broadcast a first advertisement packet via the wireless communication interface, the first advertisement packet configured to cause another central device to enter a hold off state for a period of time. The processing unit is further configured to cause the central device to wirelessly receive, during the period of time, a second advertisement packet via the wireless communication interface, the second advertisement packet sent from a medical device, and in response to receiving the second advertisement packet, establish a wireless communication session via the wireless communication interface between the central device and the medical device.

Embodiments of central device can include one or more the following features. The central device may be further configured to receive, prior to receiving the second advertisement packet, an acknowledgment from the other central device via the wireless communication interface that the other central device received the first advertisement packet. The processing unit may be further configured to cause the central device to include, in the first advertisement packet, information indicating a length of the period of time. The processing unit may be further configured to cause the central device to include, in the first advertising packet, an identifier of the medical device. The central device may further comprise a camera, and the processing unit may be further configured to cause the central device to obtain the identifier of the medical device using the camera. The processing unit may be configured to determine the triggering event has occurred by being further configured to determine a user input has been received by the central device. The processing unit may be configured to determine the triggering event has occurred by being further configured to determine a location of the central device is within a particular locale.

An example apparatus operating as a first central device, according to the description, comprises means for determining a triggering event has occurred, and means for wirelessly broadcasting a first advertisement packet in response to determining the triggering event has occurred, wherein the first advertisement packet is configured to cause a second central device to enter a hold off state for a period of time. The apparatus further comprises means for wirelessly receiving, during the period of time, a second advertisement packet, the second advertisement packet sent from a medical device, and means for establishing a wireless communication session between the first central device and the medical device in response to receiving the second advertisement packet.

Embodiments of the apparatus may further comprise one or more the following features. The apparatus may further comprise means for receiving, prior to receiving the second advertisement packet, an acknowledgment from the second central device that the second central device received the first advertisement packet. The apparatus may further comprise means for including, in the first advertisement packet, information indicating a length of the period of time. The apparatus may further comprise means for including, in the first advertisement packet, an identifier of the medical device, and optionally, image-capturing means configured to obtain the identifier of the medical device. The means for determining the triggering event has occurred may comprise means for determining a user input has been received by the first central device. The means for determining the triggering event has occurred may comprise means for determining a location of the first central device is within a particular locale.

An example non-transitory computer-readable medium, according to the description, has instructions embedded thereon, including computer code for determining, with a first central device, a triggering event has occurred, and wirelessly broadcasting a first advertisement packet in response to determining the triggering event has occurred, wherein the first advertisement packet is configured to cause a second central device to enter a hold off state for a period of time. The instructions further comprise computer code for wirelessly receiving, during the period of time, a second advertisement packet, the second advertisement packet sent from a medical device, and establishing a wireless communication session between the first central device and the medical device in response to receiving the second advertisement packet.

Embodiments of the non-transitory computer-readable medium may further comprise one or more the following features. The instructions may further comprise computer code for receiving, prior to receiving the second advertisement packet, an acknowledgment from the second central device that the second central device received the first advertisement packet. The instructions may further comprise computer code for including, in the first advertisement packet, information indicating a length of the period of time. The instructions may further comprise computer code for including, in the first advertisement packet, an identifier of the medical device. The instructions may further comprise g computer code for obtaining the identifier of the medical device using a camera of the first central device. The computer code for determining the triggering event has occurred comprises computer code for determining a user input has been received by the first central device. The computer code for determining the triggering event has occurred comprises computer code for determining a location of the first central device is within a particular locale.

BRIEF DESCRIPTION OF DRAWINGS

Non-limiting and non-exhaustive aspects are described with reference to the following figures, wherein like reference numerals refer to like parts throughout the various figures unless otherwise specified.

DETAILED DESCRIPTION

Several illustrative embodiments will now be described with respect to the accompanying drawings, which form a part hereof. The ensuing description provides embodiment(s) only, and is not intended to limit the scope, applicability or configuration of the disclosure. Rather, the ensuing description of the embodiment(s) will provide those skilled in the art with an enabling description for implementing an embodiment. It is understood that various changes may be made in the function and arrangement of elements without departing from the spirit and scope of this disclosure.

In recent years, medical devices (such as inhalers, pill packs, injector pens, skin patches, wearable monitors and sensors, etc.) have become modified with electronic modules in order to track and report related data such as date and time of usage, sensor data, method of use, etc. These "smart" medical devices can then relay this data wirelessly to a mobile device, such as a smart phone of a patient. The mobile device can then provide an analysis of the data and/or other information via a display, using, for example a software application to process the data and/or provide user interactivity. To communicate the data from the medical device to the mobile device, the medical device and mobile device may establish a wireless connection using a technology, such as BLE, that creates a central/peripheral relationship where the mobile device is the central and the medical device is the peripheral.

This central/peripheral relationship between the mobile device and the medical device can be problematic, however, in some circumstances. In BLE, for example, when a BLE central and bonded BLE peripheral are in close proximity, they can typically connect when the BLE peripheral advertises. This can prevent other devices from pairing with the BLE peripheral. Thus, if the patient using the mobile and medical devices takes the medical device to a health care provider (e.g., hospital, health clinic, Doctor's office, etc.) to transmit the data obtained by the medical device to a device of the health care provider (e.g., for evaluation by the health care provider), the medical device may not be able to establish a connection with the device of the health care provider if the patient's mobile device is nearby.

Techniques provided herein address these and other issues by enabling a tablet (or other device of a health care provider) to broadcast a "central priority" advertisement packet to the mobile device. Upon detecting the central priority advertisement packet, the mobile device can enter a "hold off" state, in which the mobile device disconnects from or discontinues attempts to connect with the medical device, for a certain the period of time. While the mobile device is in the hold off state, the device of the health care provider can then establish communication with the medical device to allow the medical device to communicate data with the device of health care provider.

Figure 5:
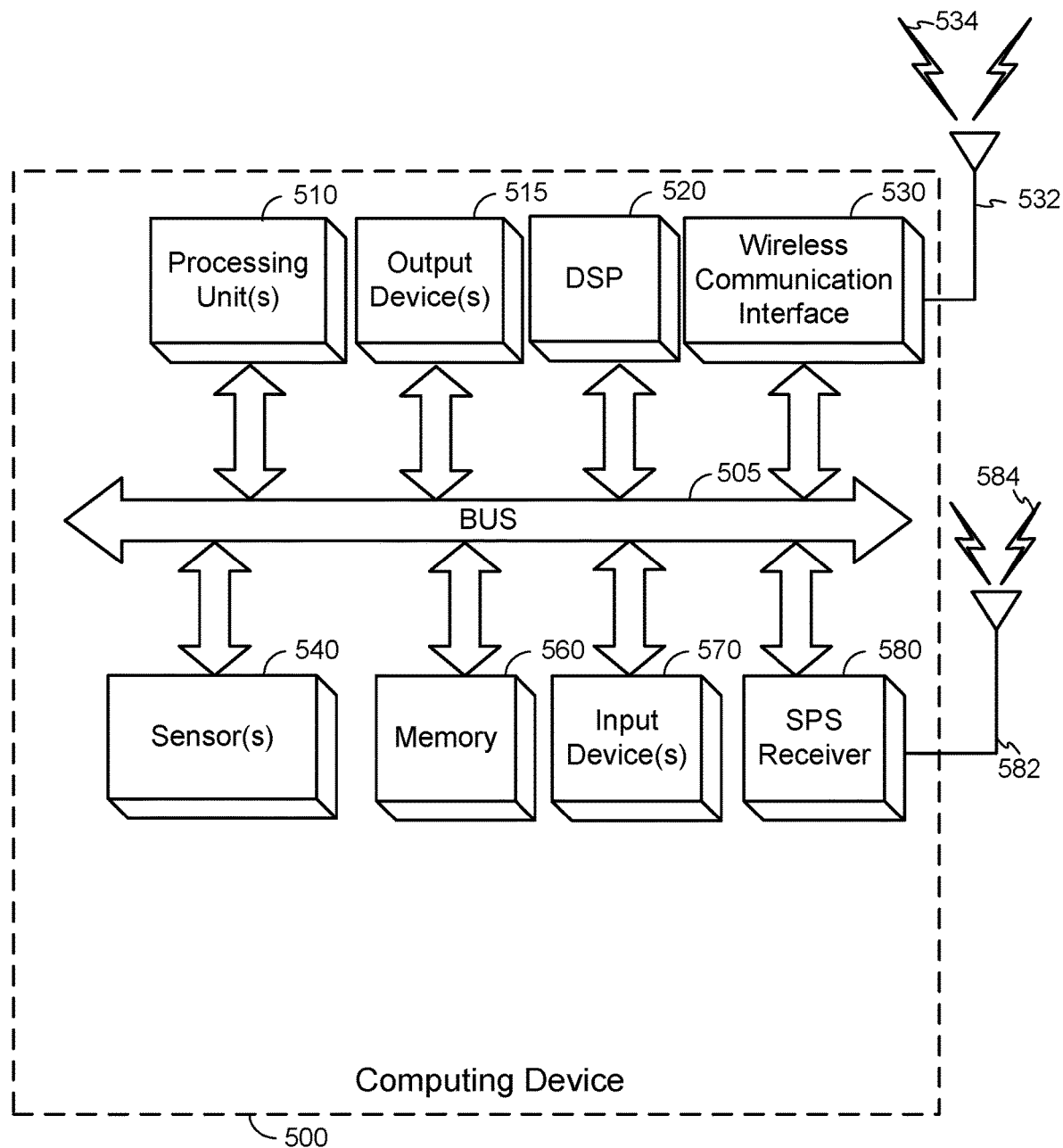
FIG. 5 is illustrates an embodiment of a computing device.

It can be noted that the techniques herein are not limited to medical devices. As such, they can be utilized in other applications using wireless communication between a peripheral device and one or more central devices. Furthermore, although devices in the embodiments provided herein may be described as mobile devices, tablets, and/or other specific types of devices, it will be understood that alternative embodiments are not so limited. The techniques described herein can be used using any of a variety of computing devices, which will be understood by a person of ordinary skill in the art. An example of a generic computing device is illustrated in FIG. 5 and discussed in detail below.

Figure 1:
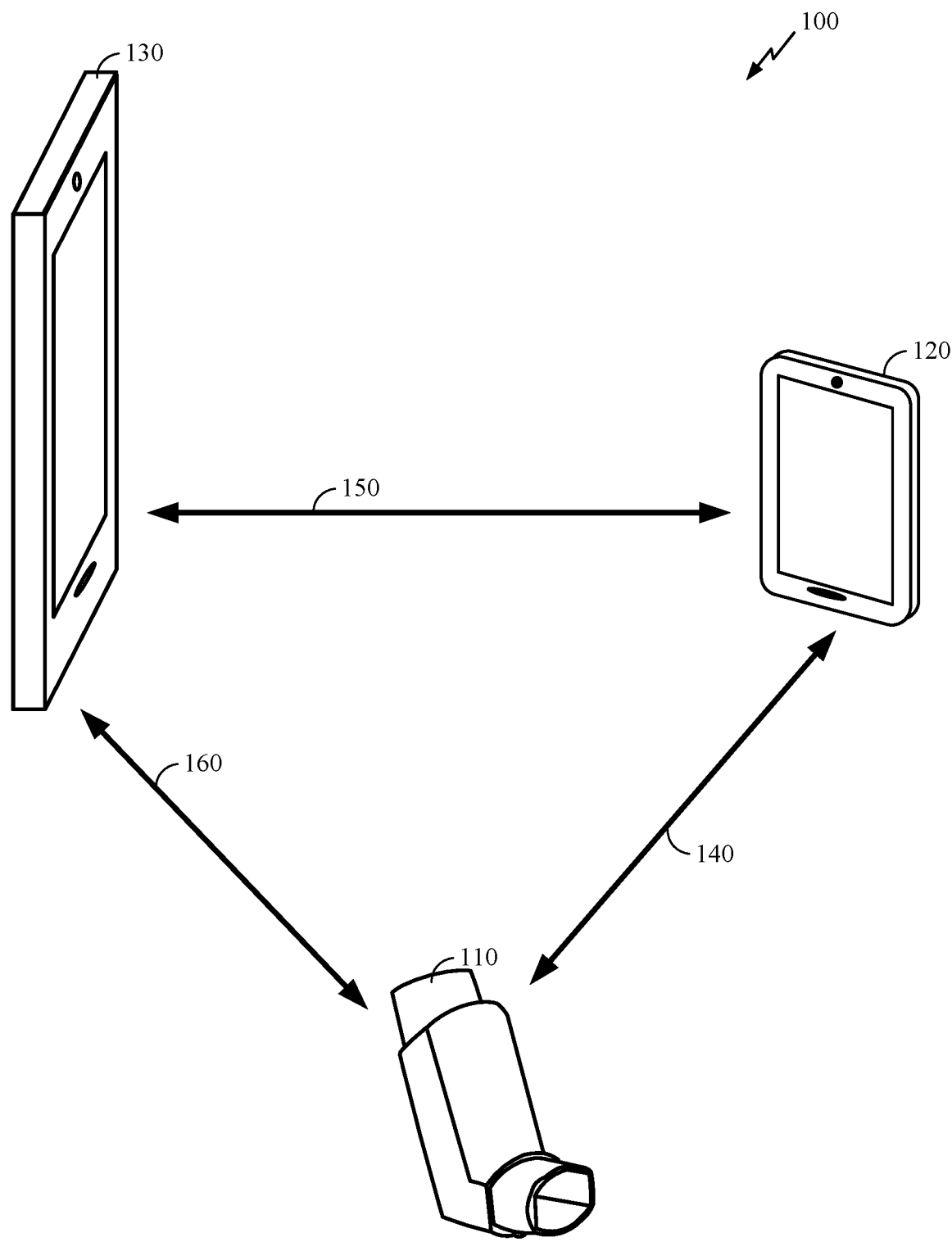
FIG. 1 is a diagram of a scenario in which a central priority advertisement packet can be used to establish a connection priority in a helpful way, according to an embodiment.

FIG. 1 is a diagram of a scenario 100 in which a central priority advertisement packet can be used to establish a connection priority in a helpful way, according to an embodiment. Here, a medical device 110, a patient's mobile device 120, and a health care provider's device 130, are illustrated as an inhaler, mobile phone, and tablet, respectively. However, will be understood that, although particular types of devices are illustrated, the types of medical, mobile, and health care devices can vary in different scenarios and depending on desired functionality. Additionally, the devices illustrated in FIG. 1 may include some or all software and/or hardware components of the computing device 500 illustrated in FIG. 5 and discussed in more detail below.

Wireless connections 140, 150, and 160 are illustrated with two-way arrows, and may comprise communication links utilizing any of a variety of wireless technologies. These technologies may include, for example, Bluetooth®, BLE, Zigbee®, Institute of Electrical and Electronics Engineers (IEEE) 802.15.4, near field communication (NFC), Wi-Fi, etc., or a proprietary solution, for example, that may utilize advertisement broadcasting in a manner similar to the embodiments described herein. Although two-way arrows suggests two-way communication, one or more of the wireless connections 140, 150, and 160 may comprise one-way communications, in some embodiments. Moreover, for a single embodiment, connections between different devices may be established using different technologies.

It will further be understood that wireless connections 140, 150, and 160 may represent established connections or preexisting relationships (e.g., a central/peripheral relationship) between components that may not require active communication. For example, once established, wireless connection 140 may enable the medical device 110 and the patient's mobile device 120 to quickly engage in an active communication session, forgoing protocol that may be required if the medical device 110 and the patient's mobile device 120 were communicating for the first time. Thus, wireless connections 140, 150, and 160 may represent connections in which devices are "paired," "bonded," "connected," and/or where establishing an active communication session between the devices is prioritized over establishing an active communication session with a device for which a wireless connection is not yet established. (It can be further noted that, in some embodiments, wireless connection 150 may not be established between the health care provider's device 130 and the patient's mobile device 120. Instead, as noted below, the health care provider's device 130 may simply broadcast information received by the patient's mobile device 120, which may not result in establishing the wireless connection 150.

Here, the medical device 110 may comprise any of a variety of types of medical devices configured to send usage and/or other data to one or more other devices. The type of data collected can vary based on device type, which may include, for example, an inhaler, skin patch, pill pack, injector pen, wearable monitor, sensor, etc. That said, the data may generally include date and/or time the medical device 110 was used, a length of time the medical device 110 was used, an estimated or calculated effectiveness of the use, and amount of medicine administered, and amount of medicine remaining, an indication of misuse of the medical device 110, and the like. The medical device 110 may therefore have hardware and/or software components such as one or more sensors, processors, memories, clocks, wireless communication interfaces, etc., to enable the collection and transmittal of data (and, according to some embodiments, some processing of the data). Again, examples of such components are illustrated in FIG. 5 and discussed in more detail below.

Medical device 110 may be used at home (or elsewhere) by a patient and may be coupled with the patient's mobile device 120 for various purposes. The patient's mobile device 120 may be a personal device (e.g., a mobile phone, tablet, personal media player, personal digital assistant, etc.) executing a software application configured to cause the patient's mobile device 120 to establish a wireless connection 140 with the medical device 110. The application may also provide additional functionality related to the medical device 110, such as providing information regarding proper use of the medical device 110, providing reminders to the patient of one to use the medical device 110, and the like.

According to some embodiments, such as those using BLE, the wireless connection 140 may establish a central-peripheral relationship between the patient's mobile device 120 and the medical device 110. In particular, the patient's mobile device 120 may be designated the central device, and the medical device 110 may be designated the peripheral device. The medical device 110 and patient's mobile device 120 may therefore communicate using the wireless connection 140 according to governing protocols for the central-peripheral relationship.

Establishing the wireless connection 140 between the mobile device and the medical device 110 may enabled on the mobile device via software (e.g., an application), firmware, and/or hardware. In some embodiments, the medical device 110 may initiate the establishment of the connection by broadcasting an advertisement packet, which itself may be triggered by an action, according to some embodiments. For example, in some embodiments, a user may press a button on the medical device 110 (or cause another detectable event to occur) to initiate the broadcasting of the advertisement packet and establishment of the connection.

As noted above, the wireless connection 140, once established, can cause the medical device 110 to treat the wireless connection 140 as an "existing" connection, causing the medical device 110 to prioritize connecting with the patient's mobile device 120 over connecting to other devices. In such situations, the medical device 110 becomes a "bonded peripheral" to the patient's mobile device 120, preventing other devices from establishing a communication session with the medical device 110.

Thus, referring again to the scenario 100 illustrated in FIG. 1, when the patient's mobile device 120 and the medical device 110 are, for example, in the same room as the health care provider's device 130, the health care provider's device 130 may not be able to establish a connection 160 with the medical device 110 because both the health care provider's device 130 and the patient's mobile device 120 may respond to advertisement packets broadcast by the medical device 110. And the medical device 110 may prioritize initiating an active communication session over the existing wireless connection 140 with the mobile device over attempts to communicate with the health care provider's device 130 (e.g., by establishing a wireless connection 160).

Put differently, a first central device may have difficulty establishing a connection (even a temporary connection) with a peripheral device if there is an existing central-peripheral relationship between the peripheral device and a second central device, and the second central device responds to an advertisement packet from the peripheral device. This is because the peripheral device may prioritize the response of the second central device over a response of the first central device, initiating a communication session with the second central device and ignoring the response of the first central device.

Techniques described herein address this and other issues by enabling a first central device (e.g. the health care provider's device 130 of FIG. 1) to broadcast a "central priority advertisement packet" that causes the second central device (e.g., the patient's mobile device 120) to ignore advertisement packets broadcast by the medical device 110 for a certain period of time. During that time, the first central device can establish a connection with the peripheral device.

Figure 2:
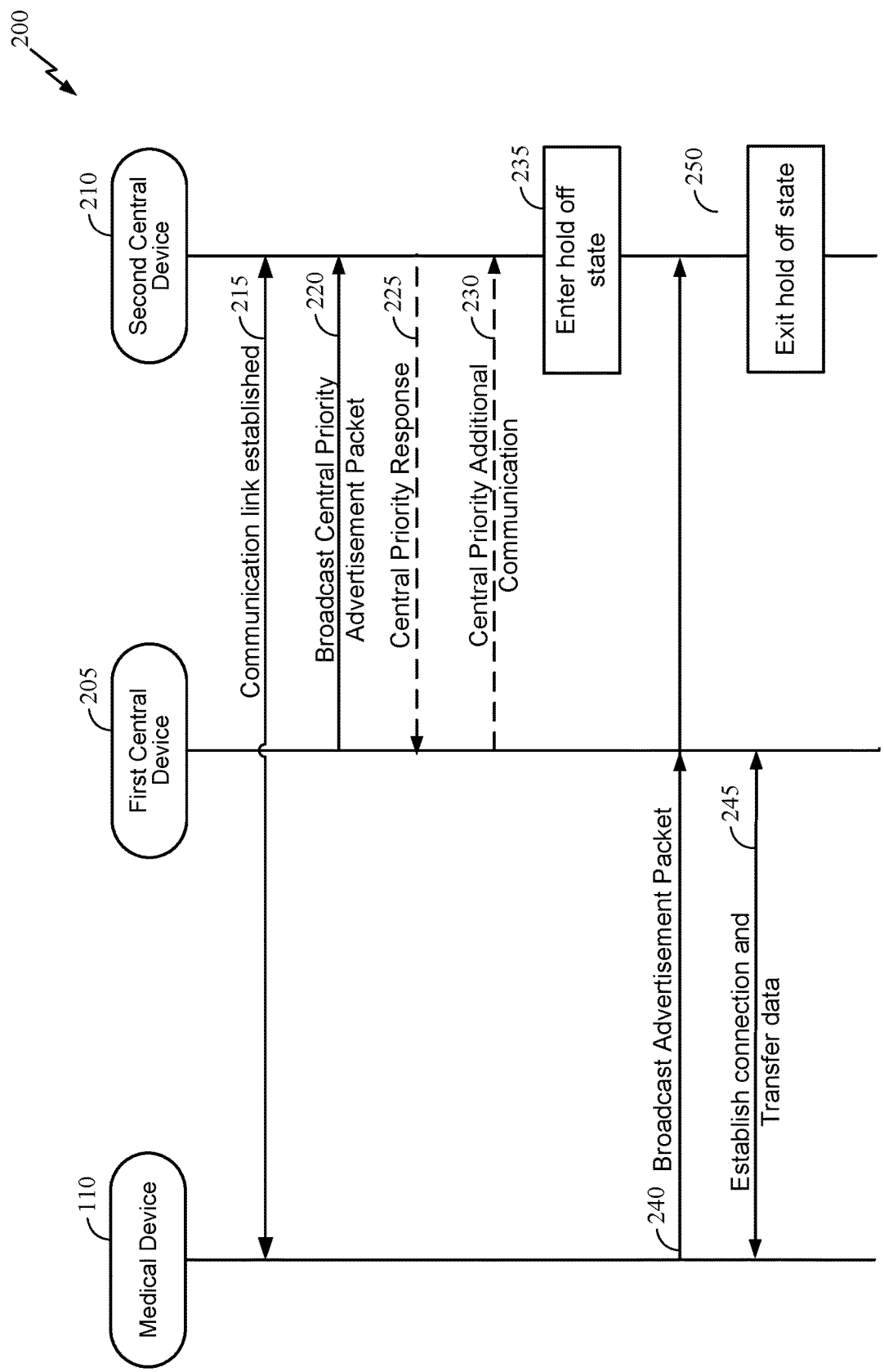
FIG. 2 is a call-flow diagram illustrating the communication that can occur between a first central device, a second central device, and a medical device relation to the broadcasting of the central priority advertisement packet, according to an embodiment.

FIG. 2 is a call-flow diagram 200 illustrating the communication that can occur between a first central device 205, a second central device 210, and a medical device 110 relation to the broadcasting of the central priority advertisement packet, according to an embodiment. Here, the first central device 205 and the second central device 210 are referred to generically, but they may correspond to the health care provider's device 130 and the patient's mobile device 120, respectively, as illustrated in FIG. 1.

The formatting content of the central priority advertisement packet can vary, depending on desired functionality. Moreover the various communications disclosed in FIG. 4 may be in accordance with applicable protocols and/or standards governed by the technologies involved in the communications. Additionally, means for performing any or all of the functions illustrated in FIG. 2 may include software and/or hardware components of a computing device, such as the computing device 500 of FIG. 5, discussed in more detail below.

At action 215, a connection is established between the medical device 110 and the second central device 210. Although illustrated immediately above action 220, it will be understood that the establishment of the connection between the medical device 110 and the second central device 210 may occur at any time previous to action 220. Here, "establishing" a connection means establishing a relationship between the medical device 110 and the second central device 210 in which the medical device 110 will prioritize communications with the second central device 210 over devices with which the medical device 110 does not have an established connection. In some embodiments, for example, this may include "connecting" the medical device 110 with the second central device 210 and/or causing the "bonding" the medical device 110 to the second central device 210 as a bonded peripheral (e.g., under BLE standards). According to some embodiments, any active communication session between the medical device 110 and the second central device 210 will have ended prior to action 220.

At action 220, the first central device 205 broadcasts a central priority advertisement packet for detection by the second central device 210 (and potentially any other central device that may respond to advertisement packets broadcast from the medical device 110). Depending on governing standards and/or protocols of the technology used, multiple central priority advertisement packets may be transmitted to ensure that that they are detected by the second central device 210. Using BLE, for example, the first central device 205 may transmit central priority advertisement packets on the three BLE pairing channels in a manner to maximize the probability that the second central device 210 will detect at least one of the central priority advertisement packets. In some embodiments, for example, the first central device 205 may send 10-20 central priority advertisement packets. In other embodiments, the tablet may send a larger or smaller number of central priority advertisement packets.

At action 225, the second central device 210 may optionally provide a central priority response, such as an acknowledgment packet (ACK), acknowledging receipt of the central priority advertisement packet. The first central device 205 and second central device 210 may then optionally engage in central priority additional communication, as illustrated at action 230, if desired. For example, in some embodiments an identifier of the medical device 110 and/or a length of time for the second central device 210 to be in a hold off state may be communicated in the central priority additional communication at action 230. (Otherwise, such information may be included in the central priority advertisement packet itself).

At action 235, the second central device 210 then enters the hold off state for a predetermined amount of time. This predetermined amount of time may be user-definable, defined by the first central device 205 (and, as indicated above, included in the central priority advertisement packet at action 220 and/or at the central priority additional communication at action 230), a static value, or the like. During this time, the second central device 210 can ignore any advertising packets broadcast by the medical device 110 (and, optionally, other devices, depending on desired functionality).

Entering the hold off state at action 235 may be orchestrated by an application executed by the second central device 210. For example, the application may be configured to parse data received via a wireless technology (e.g., BLE) and, upon receiving the central priority advertisement packet (and, optionally, any central priority additional communication from the first central device 205), restrict communications accordingly. In some embodiments, for example, the second central device 210 may ignore advertisement packets from any device during the hold off period. In other embodiments, the second central device 210 may ignore only advertisement packets from the medical device 110, which may be identified by the first central device 205 or independently via the application executed by the second central device 210 (e.g., specified in user settings). In some embodiments, the second central device 210 may only enter the hold off state if it recognizes an identifier of the medical device included in the central priority advertisement packet or central priority additional communication.

At action 240, the medical device 110 broadcasts an advertisement packet. This action may be part of a standard advertisement packet broadcasting schedule, or may be triggered by another event. As previously described, a user (e.g., the patient, a health care provider, etc.) may trigger the broadcasting of the advertisement packet by the medical device 110 by taking a predetermined action detectable by the medical device 110, such as pressing a button, flipping a switch, performing a certain gesture, or the like. The triggering action may vary, depending on factors, such as the capabilities of the medical device 110, desired functionality, etc.

Although both the first central device 205 and the second central device 210 receive the advertisement packet broadcast by the medical device at action 240, because the second central device 210 receives the advertisement packet while in the hold off state, it will not respond to the advertisement packet. However, the first central device 205 can then, at action 245, establish a connection with the medical device 110 and transfer data. The action at 245 may comprise, depending on desired functionality, pairing the first central device 205 and the medical device 110 to exchange information securely in a communication session. Initiating the communication session may occur prior to the second central device exiting the hold off state at action 250, so that the second central device 210 does not attempt to initiate a communication session with the medical device 110. However, the remainder of the communication session (during which the medical device 110 may not broadcast any advertisement packets) may occur during or after the second central device 210 exits the hold off state.

The connection type (e.g., temporary or more permanent) of the connection at action 245 may be determined by an application executed by the first central device 205. Once the first central device 205 and the medical device 110 complete their communications, the first central device 205 and can release the medical device 110, enabling the medical device 110 to connect with other devices (such as the second central device 210).

It can be noted that the way in which the hold off state is managed may vary, depending on desired functionality. As noted above, the second central device 210 may enter a hold off state for a predetermined amount of time. In other embodiments, the central priority advertisement packet may cause the second central device 210 to enter a hold off state or otherwise terminate a connection with the medical device 110 until the second central device 210 receives a second message. For example, in some embodiments, after the data is transferred at action 245 and the communication between the first central device 205 and medical device 110 is terminated, the first central device 205 can then send a message to the second central device 210 enabling the second central device 210 device to resume communications with the medical device 110 or otherwise exit the hold off state.

Figure 3:
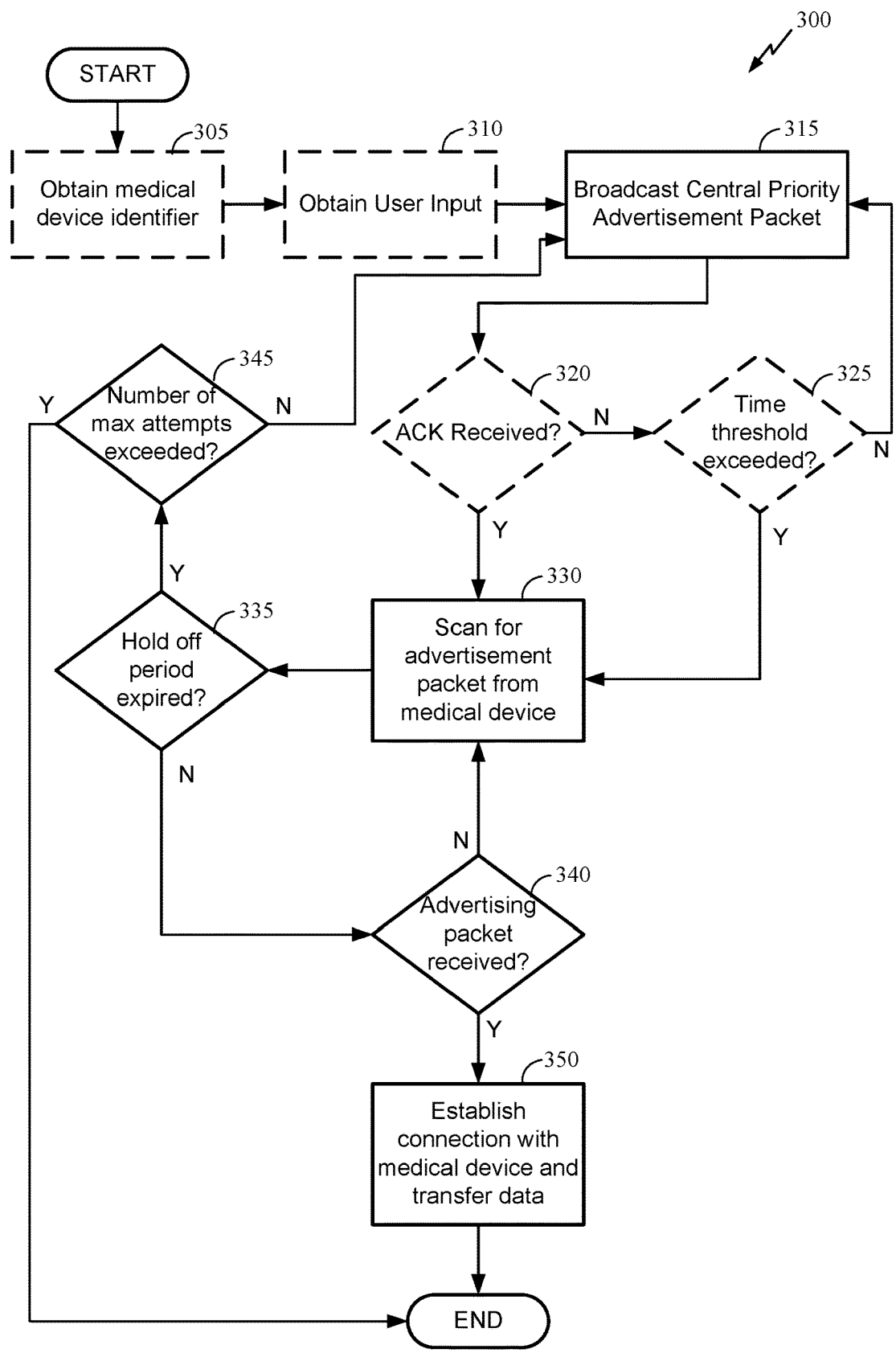
FIG. 3 is a flowchart illustrating a method of enabling connection priority determination and the medical device, according to an embodiment.

FIG. 3 is a flowchart 300 illustrating a method of enabling connection priority determination and the medical device, according to an embodiment. Here, the elements of the flowchart 300 illustrate functions that can be performed by a first central device attempting to establish a connection with the medical device. As such, some of the functionality may overlap with the functionality of the first central device 205 illustrated in FIG. 2. However, it will be understood that embodiments may employ different combinations or other variations of what is illustrated and described in these figures.

The process may optionally begin at function 305, where the medical device identifier is obtained. As indicated above, the first central device may provide a second central device (e.g., in a central priority advertisement packet broadcast or related communications) an identifier of the medical device with which the first central device is to connect. This identifier may be obtained using, for example, a Quick Response (QR) code, barcode, serial code, or other identifier of the medical device, which may be indicated on the medical device itself. According to some embodiments, the first central device may include a camera or other sensor configured to capture this identifier. (A camera, for example, may be able to determine a visual identifier located on the medical device.) Alternatively, a user may be able to manually enter the identifier of the medical device into the first central device (e.g., using a keyboard, touchscreen, or other input device). Depending on desired functionality, the identifier of the peripheral device may be globally unique, or relatively unique (e.g., compared to identifiers other devices in the area).

At function 310, user input is obtained. Here, too, this action may be optional, depending on desired functionality. Moreover, in some embodiments it may be combined with obtaining the medical device identifier at function 305. User input may be obtained and used as a trigger to initiate the communication between the first central device and the medical device (by first broadcasting a central priority advertisement packet, as indicated at function 315). User input can be provided in any of a variety of ways, depending on desired functionality. In some embodiments, a user input may simply comprise pressing a button on a touchscreen of the first central device. In some embodiments, the user may be able to specify a length of time for the mobile device to be in a hold off state, which may be included in a central priority advertisement packet or related communication.

Although user input can trigger the functionality at function 315 (broadcasting the central priority advertisement packet), embodiments may utilize additional or alternative triggers. For instance, in some embodiments, the tablet may be configured to periodically transmit the central priority advertisement packet at a relatively high frequency, thereby enabling the tablet to quickly establish a connection with the peripheral device. Moreover, in some embodiments, the tablet may be configured to send the central priority advertisement packet in this periodic fashion only when the tablet determines it is within a particular area or locale (e.g., a doctor's office, hospital, health clinic, etc.)

At function 315, the central priority advertisement packet is broadcast. Here, the central priority advertisement packet may be configured to cause a second central device to enter a hold off state for a predetermined amount of time, as indicated above. Because this functionality may be implemented at the application layer, an application executed by the first central device and the same or similar application executed by the second central device may determine what information is included in the central priority advertisement packet. This information, which may be parsed by the second central device after receiving the packet, may include the identifier of the medical device, a length of time for the second device to be in the hold off state, and/or other information. Moreover, devices that are not executing applications configured to react to the central priority advertisement packet will simply disregard the central priority advertisement packet.

Optionally, where an acknowledgment message (ACK) is expected from a second central device, the first central device can determine whether the ACK is received at function 320. If it is not received, the can be determined whether a time threshold for broadcasting the central priority advertisement packet has been exceeded, at function 325. If not, the central priority advertisement packet may again be broadcast at action 315. However, if the time threshold has been exceeded (which may be the case where the central priority advertisement packet has been broadcast several times with no ACK response), or if the ACK response is received, the process can move to function 330, where the advertisement packet from the medical device is received. (As indicated in FIG. 2, if an ACK is received from a second central device, the first central device may first provide additional information to the second central device, in some embodiments.)

Functions 335-345 illustrate one technique of awaiting the advertisement packet from the medical device. Here, at function 335, the first central device determines whether the hold off period has expired. If not, the process then moves to function 340, where the first central device determines whether the advertising packet is received. It continues to scan until either the hold off period does expire or the advertisement packet is received. If the hold off period expires before an advertisement packet is received, the process moves to function 345, where it is determined whether a maximum number of attempts is exceeded. If not, the first central device can return to function 315, where it again broadcasts the central priority advertisement packet. Otherwise, if the maximum number of attempts has exceeded, the process ends. Embodiments that enable multiple attempts in this manner can extend the window of time for users to coordinate providing any user input to the first central device (at function 310), providing a triggering event and the medical device (e.g., pressing a button), and allowing the two devices to initiate a communication session. Of course, alternative embodiments may extend the hold off period or implement alternative functionality.

If the advertising packet is received from the medical device, then the first central device can establish a connection with the medical device and transfer data, at function 350. This functionality may include establishing a central/peripheral relationship using paring and/or similar protocol. The transfer of data may be performed in a communication session, and may include transferring data (e.g., usage data) from the medical device to the first central device, enabling the first central device to process the data and/or relay it to another device/system. At the end of the data transfer, the first central device may terminate the established connection with the medical device to enable to enable the medical device to reengage in normal communications with the second central device (and/or other devices).

Figure 4:
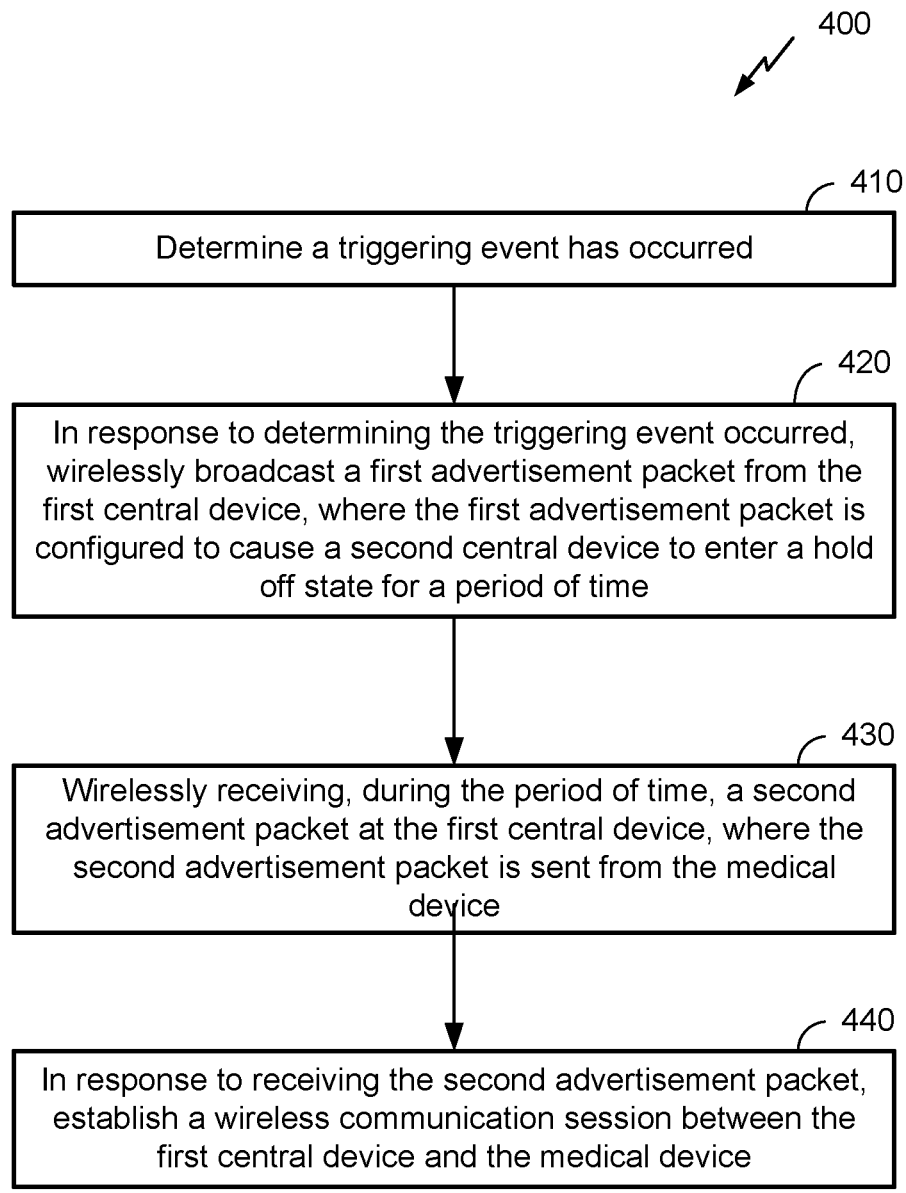
FIG. 4 is a flow diagram illustrating a method of enabling connection priority determination in a medical device, according to another embodiment.

FIG. 4 is a flow diagram 400 illustrating a method of enabling connection priority determination in a medical device, according to another embodiment. In some embodiments, the medical device may not be actively communicating with another device. Similar to FIG. 3, the functionality of the blocks in the flow diagram 400 illustrate functions that may be performed by a first central device. A first central device may comprise a computing device, and thus means for performing the functions of one or more of the blocks in the flow diagram 400 may comprise hardware and/or software components of a computing device, such as the computing device 500 illustrated in FIG. 5, described in more detail below.

In this embodiment, the method may begin at block 410, it is determined that a triggering event has occurred. As indicated previously, a triggering event may comprise receiving user input at a first central device. The user input may vary, depending on the functionality of the first central device and/or application executed thereby. For instance, according to some embodiments, a user (e.g., health care provider) may evoke a graphical user interface of an application executed by the first central device, which may be illustrated on a touchscreen of the first central device. The user may then press a button on the graphical user interface prompting the first mobile device to attempt to communicate with a nearby medical device. Other triggering events may include the first central device being located within a particular locale, the first central device receiving a wireless communication, sensor input, or the like. Means for performing the functionality at block 410 may comprise, for example, sensor(s) 540, input device(s) 570, wireless communication interface 530, and/or other components of a computing device, such as the computing device illustrated in FIG. 5 and described in further detail below.

The functionality at block 420 comprises, in response to determining the triggering event occurred, wirelessly broadcasting a first advertisement packet from the first central device. Here, the first advertisement packet may be a central priority advertisement packet that is configured to cause a second central device to enter a hold off state for a period of time. According to some embodiments, the first advertisement packet may specify a length of this period of time, which may be user configurable (enabling a user to indicate how long they may want to attempt to communicatively connected the first central device with the medical device). Additionally or alternatively, the first advertisement packet may include an identifier of the medical device. In some embodiments, this may mean obtaining the identifier of the medical device using a camera, which may capture a visible identifier (such as a QR code). Means for performing the functionality at block 420 may comprise, for example, processing unit(s) 510, memory 560, bus 505, wireless communication interface 530, and/or other components of a computing device, such as the computing device illustrated in FIG. 5 and described in further detail below.

At block 430, a second advertisement packet is wirelessly received at the first central device during the period of time. Here, the second advertisement packet is sent from the medical device. This can be an advertisement packet to enable the first central device to initiate a communication session with the medical device. As noted above, in some embodiments, prior to receiving the second advertisement packet, an acknowledgment may be received from the second central device that the second central device has received the first advertisement packet. Means for performing the functionality at block 430 may comprise, for example, processing unit(s) 510, memory 560, bus 505, wireless communication interface 530, and/or other components of a computing device, such as the computing device illustrated in FIG. 5 and described in further detail below.

At block 440, in response to receiving the second advertisement packet, a wireless communication session is established between the first central device at the medical and device. Thus, according to some embodiments, the first central device may respond to the second advertisement packet according to proper protocol to initiate the communication session. This may mean pairing or otherwise creating a wireless connection or connection with the medical device to enable the medical device to provide usage data and/or other information to the first central device. Means for performing the functionality at block 440 may comprise, for example, processing unit(s) 510, memory 560, bus 505, wireless communication interface 530, and/or other components of a computing device, such as the computing device illustrated in FIG. 5 and described in further detail below.

FIG. 5 illustrates an embodiment of a computing device 500, all or part of which can be utilized in the embodiments provided herein as, for example, a central device, peripheral device, health care provider's device, patient's device, medical device, and/or other devices described herein. FIG. 5 is meant only to provide a generalized illustration of various components, any or all of which may be included or omitted in a particular type of device as appropriate. It can be noted that, in some instances, components illustrated by FIG. 5 can be localized to a single physical device and/or distributed among various networked devices, which may be disposed at different physical locations. The computing device 500 may be configured to execute one or more functions of the methods described herein.

The computing device 500 is shown comprising hardware elements that can be electrically coupled via a bus 505 (or may otherwise be in communication, as appropriate). The hardware elements may include a processing unit(s) 510 which may comprise without limitation one or more general-purpose processors, one or more special-purpose processors (such as digital signal processing (DSP) chips, graphics acceleration processors, application specific integrated circuits (ASICs), and/or the like), and/or other processing structure or means, which can be configured to perform one or more of the methods described herein. As shown in FIG. 5, some embodiments may have a separate DSP 520, depending on desired functionality. The computing device 500 also may comprise one or more input devices 570, which may comprise without limitation one or more touch screens, touch pads, microphones, buttons, dials, switches, and/or the like, which may provide for user input, for example. Output devices 515 may comprise, without limitation, one or more displays, light emitting diode (LED)s, speakers, and/or the like.

The computing device 500 might also include a wireless communication interface 530, which may comprise without limitation a modem, a network card, an infrared communication device, a wireless communication device, and/or a chipset enabling communications using, for example, Bluetooth®, BLE, IEEE 802.11, IEEE 802.15.4 (ZIGBEE®), Wi-Fi, a WiMAX™ device, cellular communication, and/or the like. The wireless communication interface 530 may permit data to be communicated with a network, computer system, and/or any other electronic device as described herein. The communication can be carried out via one or more wireless communication antenna(s) 532 that send and/or receive wireless signals 534.

Depending on desired functionality, the wireless communication interface 530 may comprise separate transceivers to communicate with different devices, which may be on different networks. These different data networks may comprise various network types. A wireless wide area network (WWAN), for example, may be a Code Division Multiple Access (CDMA) network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, a WiMax (IEEE 802.16), and so on. A CDMA network may implement one or more radio access technologies (RATs) such as cdma2000, Wideband-CDMA (W-CDMA), and so on. Cdma2000 includes IS-95, IS-2000, and/or IS-856 standards. A TDMA network may implement Global System for Mobile Communications (GSM), Digital Advanced Mobile Phone System (D-AMPS), or some other RAT. An OFDMA network may employ Long-Term Evolution (LTE), LTE Advanced, and so on. LTE, LTE Advanced, GSM, and W-CDMA are described in documents from 3rd Generation Partnership Project (3GPP). Cdma2000 is described in documents from a consortium named "3rd Generation Partnership Project 2" (3GPP2). 3GPP and 3GPP2 documents are publicly available. A wireless local area network (WLAN) may also be an IEEE 802.11x network, and a wireless personal area network (WPAN) may be a Bluetooth® network, an IEEE 802.15x, or some other type of network. The techniques described herein may also be used for any combination of WWAN, WLAN and/or WPAN.

The computing device 500 can further include sensor(s) 540, which may vary depending on the type of computing device. Such sensors may comprise, without limitation, IMUs (e.g., accelerometer(s), gyroscope(s), etc.) cameras, magnetometers and/or other compasses, altimeters, microphones, proximity sensors, light sensors, and the like. In some embodiments, the sensor(s) 540 may additionally or alternatively include health-related sensors, such as sensors configured to detect a user's vital signs (and/or other health information), use of a medical product orientation and/or configuration of the product while used, etc.

Embodiments of the computing device 500 may also include a satellite positioning system (SPS) receiver 580 capable of receiving signals 584 from one or more SPS satellites using an SPS antenna 582, and being powered on and off in the manner described in the embodiments provided herein. Such positioning can be utilized to complement and/or incorporate the techniques described herein. The SPS receiver 580 can extract a position of the computing device 500, using conventional techniques, from SPS satellite vehicles (SVs) of a global navigation satellite system (GNSS), such as Galileo, GLONASS, Compass, Quasi-Zenith Satellite System (QZSS) over Japan, Indian Regional Navigational Satellite System (IRNSS) over India, Beidou over China, and/or any other GNSS. Moreover, the SPS receiver 580 can be used various augmentation systems (e.g., a Satellite Based Augmentation System (SBAS)) that may be associated with or otherwise enabled for use with one or more global and/or regional navigation satellite systems. By way of example but not limitation, an SBAS may include an augmentation system(s) that provides integrity information, differential corrections, etc., such as, e.g., Wide Area Augmentation System (WAAS), European Geostationary Navigation Overlay Service (EGNOS), Multi-functional Satellite Augmentation System (MSAS), Global Positioning System (GPS) Aided Geo Augmented Navigation or GPS and Geo Augmented Navigation system (GAGAN), and/or the like. Thus, as used herein an SPS may include any combination of one or more global and/or regional navigation satellite systems and/or augmentation systems, and SPS signals may include SPS, SPS-like, and/or other signals associated with such one or more SPSes.

The computing device 500 may further include and/or be in communication with a memory 560. The memory 560 may comprise, without limitation, local and/or network accessible storage, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like. This memory 560 may be used to store the images (or frames) captured by the forward-facing camera as described herein.

The memory 560 of the computing device 500 also can comprise software elements (not shown), including an operating system, device drivers, executable libraries, and/or other code, such as one or more application programs, which may comprise computer programs provided by various embodiments, and/or may be designed to implement methods, and/or configure systems, provided by other embodiments, as described herein. Merely by way of example, one or more procedures described with respect to the functionality discussed above might be implemented as computer code and/or instructions executable by the computing device 500 (and/or processing unit(s) 510 within a computing device 500). In an aspect, then, such code and/or instructions can be used to configure and/or adapt a general purpose computer (or other device) to perform one or more operations in accordance with the described methods. The memory 560 may therefore comprise non-transitory machine-readable media having the instructions and/or computer code embedded therein/thereon. Common forms of computer-readable media include, for example, magnetic or optical media, a RAM, a PROM, EPROM, a FLASH-EPROM, any other memory chip or cartridge, a carrier wave as described hereinafter, or any other medium from which a computer can read instructions and/or code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

The methods, systems, and devices discussed herein are examples. Various embodiments may omit, substitute, or add various procedures or components as appropriate. For instance, features described with respect to certain embodiments may be combined in various other embodiments. Different aspects and elements of the embodiments may be combined in a similar manner. The various components of the figures provided herein can be embodied in hardware and/or software. Also, technology evolves and, thus, many of the elements are examples that do not limit the scope of the disclosure to those specific examples.

Reference throughout this specification to "one example", "an example", "certain examples", or "exemplary implementation" means that a particular feature, structure, or characteristic described in connection with the feature and/or example may be included in at least one feature and/or example of claimed subject matter. Thus, the appearances of the phrase "in one example", "an example", "in certain examples" or "in certain implementations" or other like phrases in various places throughout this specification are not necessarily all referring to the same feature, example, and/or limitation. Furthermore, the particular features, structures, or characteristics may be combined in one or more examples and/or features.

Some portions of the detailed description included herein are presented in terms of algorithms or symbolic representations of operations on binary digital signals stored within a memory of a specific apparatus or special purpose computing device or platform. In the context of this particular specification, the term specific apparatus or the like includes a general purpose computer once it is programmed to perform particular operations pursuant to instructions from program software. Algorithmic descriptions or symbolic representations are examples of techniques used by those of ordinary skill in the signal processing or related arts to convey the substance of their work to others skilled in the art. An algorithm is here, and generally, is considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals, or the like. It should be understood, however, that all of these or similar terms are to be associated with appropriate physical quantities and are merely convenient labels. Unless specifically stated otherwise, as apparent from the discussion herein, it is appreciated that throughout this specification discussions utilizing terms such as "processing," "computing," "calculating," "determining" or the like refer to actions or processes of a specific apparatus, such as a special purpose computer, special purpose computing apparatus or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

In the preceding detailed description, numerous specific details have been set forth to provide a thorough understanding of claimed subject matter. However, it will be understood by those skilled in the art that claimed subject matter may be practiced without these specific details. In other instances, methods and apparatuses that would be known by one of ordinary skill have not been described in detail so as not to obscure claimed subject matter.

The terms, "and", "or", and "and/or" as used herein may include a variety of meanings that also are expected to depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein may be used to describe any feature, structure, or characteristic in the singular or may be used to describe a plurality or some other combination of features, structures or characteristics. Though, it should be noted that this is merely an illustrative example and claimed subject matter is not limited to this example.

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein.

Therefore, it is intended that claimed subject matter not be limited to the particular examples disclosed, but that such claimed subject matter may also include all aspects falling within the scope of appended claims, and equivalents thereof.

What is claimed is:

1. A method of enabling connection priority determination in a medical device, the method comprising:
    determining, with a first central device, a triggering event has occurred, wherein the triggering event is a user-initiated action at the medical device;
    in response to determining the triggering event has occurred, wirelessly broadcasting a first advertisement packet from the first central device, the first advertisement packet configured to cause a second central device to enter a hold off state for a period of time;
    wirelessly receiving, during the period of time, a second advertisement packet at the first central device, the second advertisement packet sent from the medical device; and
    in response to receiving the second advertisement packet, establishing a wireless communication session between the first central device and the medical device.

2. The method of claim 1, further comprising receiving at the first central device, prior to receiving the second advertisement packet, an acknowledgment from the second central device that the second central device received the first advertisement packet.

3. The method of claim 1, wherein the first advertisement packet includes information indicating a length of the period of time.

4. The method of claim 1, wherein the first advertisement packet includes an identifier of the medical device.

5. The method of claim 4, further comprising obtaining the identifier of the medical device using a camera of the first central device.

6. The method of claim 1, wherein determining the triggering event has occurred further comprises determining a user input has been received by the first central device.

7. The method of claim 1, wherein determining the triggering event has occurred further comprises determining a location of the first central device is within a particular locale.

8. A central device comprising:
a wireless communication interface;
a memory; and
a processing unit communicatively coupled with the wireless communication interface and the memory and configured to cause the central device to:
determine a triggering event has occurred, wherein the triggering event is location of the central device within a particular locale;
in response to determining the triggering event has occurred, wirelessly broadcast a first advertisement packet via the wireless communication interface, the first advertisement packet configured to cause another central device to enter a hold off state for a period of time;
wirelessly receive, during the period of time, a second advertisement packet via the wireless communication interface, the second advertisement packet sent from a medical device; and
in response to receiving the second advertisement packet, establish a wireless communication session via the wireless communication interface between the central device and the medical device.

9. The central device of claim 8, wherein the central device is further configured to receive, prior to receiving the second advertisement packet, an acknowledgment from the other central device via the wireless communication interface that the other central device received the first advertisement packet.

10. The central device of claim 8, wherein the processing unit is further configured to cause the central device to include, in the first advertisement packet, information indicating a length of the period of time.

11. The central device of claim 8, wherein the processing unit is further configured to cause the central device to include, in the first advertising packet, an identifier of the medical device.

12. The central device of claim 11, further comprising a camera, wherein the processing unit is further configured to cause the central device to obtain the identifier of the medical device using the camera.

13. The central device of claim 8, wherein the processing unit is configured to determine the triggering event has occurred by being further configured to determine a user input has been received by the central device.

14. The central device of claim 8, wherein the processing unit is configured to determine the triggering event has occurred by being further configured to determine a location of the central device is within a particular locale.

15. An apparatus for operating as a first central device, the apparatus comprising:
means for determining a triggering event has occurred, wherein the triggering event is a user-initiated action at a medical device;
means for wirelessly broadcasting a first advertisement packet in response to determining the triggering event has occurred, wherein the first advertisement packet is configured to cause a second central device to enter a hold off state for a period of time;
means for wirelessly receiving, during the period of time, a second advertisement packet, the second advertisement packet sent from the medical device; and
means for establishing a wireless communication session between the first central device and the medical device in response to receiving the second advertisement packet.

16. The apparatus of claim 15, further comprising means for receiving, prior to receiving the second advertisement packet, an acknowledgment from the second central device that the second central device received the first advertisement packet.

17. The apparatus of claim 15, further comprising means for including, in the first advertisement packet, information indicating a length of the period of time.

18. The apparatus of claim 15, further comprising means for including, in the first advertisement packet, an identifier of the medical device.

19. The apparatus of claim 18, further comprising image-capturing means configured to obtain the identifier of the medical device.

20. The apparatus of claim 15, wherein the means for determining the triggering event has occurred comprises means for determining a user input has been received by the first central device.

21. The apparatus of claim 15, wherein the means for determining the triggering event has occurred comprises means for determining a location of the first central device is within a particular locale.

22. An non-transitory computer-readable medium having instructions embedded thereon, the instructions including computer code for:
determining, with a first central device, a triggering event has occurred, wherein the triggering event is a user-initiated action at a medical device;
wirelessly broadcasting a first advertisement packet in response to determining the triggering event has occurred, wherein the first advertisement packet is configured to cause a second central device to enter a hold off state for a period of time;
wirelessly receiving, during the period of time, a second advertisement packet, the second advertisement packet sent from the medical device; and
establishing a wireless communication session between the first central device and the medical device in response to receiving the second advertisement packet.

23. The non-transitory computer-readable medium of claim 22, further comprising computer code for receiving, prior to receiving the second advertisement packet, an acknowledgment from the second central device that the second central device received the first advertisement packet.

24. The non-transitory computer-readable medium of claim 22, further comprising computer code for including, in the first advertisement packet, information indicating a length of the period of time.

25. The non-transitory computer-readable medium of claim 22, further comprising computer code for including, in the first advertisement packet, an identifier of the medical device.

26. The non-transitory computer-readable medium of claim 25, further comprising computer code for obtaining the identifier of the medical device using a camera of the first central device.

27. The non-transitory computer-readable medium of claim 22, wherein the computer code for determining the triggering event has occurred comprises computer code for determining a user input has been received by the first central device.

28. The non-transitory computer-readable medium of claim 22, wherein the computer code for determining the triggering event has occurred comprises computer code for determining a location of the first central device is within a particular locale.

29. A central device comprising:
a wireless communication interface;
a memory; and
a processing unit communicatively coupled with the wireless communication interface and the memory and configured to cause the central device to:
  determine a triggering event has occurred, wherein the triggering event is a user-initiated action at a medical device;
  in response to determining the triggering event has occurred, wirelessly broadcast a first advertisement packet via the wireless communication interface, the first advertisement packet configured to cause another central device to enter a hold off state for a period of time;
  wirelessly receive, during the period of time, a second advertisement packet via the wireless communication interface, the second advertisement packet sent from the medical device; and
  in response to receiving the second advertisement packet, establish a wireless communication session via the wireless communication interface between the central device and the medical device.

30. The central device of claim 29, further comprising receiving at the central device, prior to receiving the second advertisement packet, an acknowledgment from the another central device that the another central device received the first advertisement packet.

31. The central device of claim 29, wherein the first advertisement packet includes information indicating a length of the period of time.

32. The central device of claim 29, wherein the first advertisement packet includes an identifier of the medical device.

33. The central device of claim 32, wherein the identifier of the medical device is obtained using a camera of the first central device.

* * * * *